United States Patent
Soykan et al.

(10) Patent No.: US 7,622,303 B2
(45) Date of Patent: Nov. 24, 2009

(54) METHODS FOR IDENTIFYING PATIENTS AT RISK FOR LIFE THREATENING ARRHYTHMIAS

(75) Inventors: Orhan Soykan, Shoreview, MN (US); Timothy H. Robinson, Savage, MN (US); Walter H. Olson, North Oaks, MN (US); Vinod Sharma, Blaine, MN (US); Amy C. Dearking, Rochester, MN (US)

(73) Assignee: Medtronic, Inc., Minneapolis, MN (US)

( * ) Notice: Subject to any disclaimer, the term of this patent is extended or adjusted under 35 U.S.C. 154(b) by 756 days.

(21) Appl. No.: 11/050,611

(22) Filed: Feb. 3, 2005

(65) Prior Publication Data

US 2005/0177196 A1 Aug. 11, 2005

Related U.S. Application Data

(60) Provisional application No. 60/542,004, filed on Feb. 5, 2004.

(51) Int. Cl.
*G01N 33/00* (2006.01)

(52) U.S. Cl. .................. 436/56; 435/69.1; 435/366; 435/320.1

(58) Field of Classification Search .................. 436/56; 435/69.1, 366, 320.1
See application file for complete search history.

(56) References Cited

U.S. PATENT DOCUMENTS

| | | | |
|---|---|---|---|
| 5,018,067 A | 5/1991 | Mohlenbrock | |
| 5,437,285 A | 8/1995 | Verrier | |
| 6,099,469 A | 8/2000 | Armstrong et al. | |
| 6,210,976 B1 | 4/2001 | Sabbadini | |
| 6,274,332 B1 | 8/2001 | Keating | |
| 6,306,087 B1 | 10/2001 | Barnhill | |
| 6,368,823 B1 | 4/2002 | Brill et al. | |
| 6,432,644 B1 | 8/2002 | Keating | |
| 6,458,542 B1 | 10/2002 | George, Jr. et al. | |
| 6,500,630 B2 | 12/2002 | Conover | |
| 6,571,129 B2 | 5/2003 | Schaldach | 607/62 |
| 6,597,952 B1 | 7/2003 | Mika | |

(Continued)

FOREIGN PATENT DOCUMENTS

EP  0842475  2/1997

(Continued)

OTHER PUBLICATIONS

Arrell et al., Cardiovascular Proteomics, Evolution and Potential, Circulation Research, 88:763-773, 2001.

(Continued)

*Primary Examiner*—Sam P Siefke
(74) *Attorney, Agent, or Firm*—Hahn & Voight PLLC; Roger C. Hahn

(57) ABSTRACT

In general, the invention is directed to systems and techniques for assessing a risk of ventricular tachyarrhythmia in a patient by measuring one or more biochemical markers that reflect the health of a patient. Typically, the patient submits a sample, such as a blood sample, which is tested for one or more biomarkers. Based upon the results of the tests, the patient's risk of ventricular tachyarrhythmia may be assessed. When the patient is found to be at risk, the patient may receive an implantable medical device or drug therapy to address the risk.

24 Claims, 6 Drawing Sheets

U.S. PATENT DOCUMENTS

| | | |
|---|---|---|
| 6,647,341 B1 | 11/2003 | Golub |
| 7,208,273 B2 | 4/2007 | Keating |
| 2002/0049772 A1 | 4/2002 | Rienhoff, Jr. |
| 2002/0059030 A1 | 5/2002 | Otworth et al. ............... 702/19 |
| 2002/0076809 A1 | 6/2002 | Steinmeyer et al. |
| 2002/0077470 A1 | 6/2002 | Walker |
| 2002/0086297 A1 | 7/2002 | Siffert |
| 2002/0115073 A1 | 8/2002 | Papadopoulos |
| 2002/0155539 A1 | 10/2002 | Ruben et al. |
| 2002/0165161 A1 | 11/2002 | Allison |
| 2002/0182599 A1 | 12/2002 | Fishman ...................... 435/6 |
| 2003/0004402 A1 | 1/2003 | Hitt |
| 2003/0096782 A1 | 5/2003 | Bristow |
| 2003/0108924 A1 | 6/2003 | George, Jr. et al. |
| 2003/0162192 A1 | 8/2003 | Sotos |
| 2003/0175795 A1 | 9/2003 | Walker |
| 2003/0198970 A1 | 10/2003 | Roberts |
| 2003/0228565 A1 | 12/2003 | Oestreicher |
| 2003/0235838 A1 | 12/2003 | Keating |

FOREIGN PATENT DOCUMENTS

| | | |
|---|---|---|
| EP | 0 721 786 B1 | 3/1998 |
| EP | 1100825 B1 | 2/2000 |
| EP | 1176197 A1 | 1/2002 |
| EP | 1 480 251 A2 | 11/2004 |
| WO | 95/15116 | 6/1995 |
| WO | 96/28537 | 9/1996 |
| WO | 98/09226 | 3/1998 |
| WO | WO 99/27140 | 3/1999 |
| WO | 99/51778 A1 | 10/1999 |
| WO | WO 99/51778 | 10/1999 |
| WO | WO 99/67628 | 12/1999 |
| WO | 01/81895 A2 | 11/2001 |
| WO | 01/92567 A2 | 12/2001 |
| WO | WO 02/052033 | 7/2002 |
| WO | 02/086447 A2 | 10/2002 |
| WO | WO 03/002757 | 1/2003 |
| WO | WO 03/006687 | 1/2003 |
| WO | 03/040407 A2 | 5/2003 |
| WO | WO 2004/005931 | 1/2004 |

OTHER PUBLICATIONS

Diamandis, Eleftherios P., Proteomic Patterns in Biological Fluids: Do They Represent the Future of Cancer Diagnostics?, Clinical Chemistry, 49(8):1272-1278, 2003.

Kiernan et al., Comparative Urine Protein Phenotyping Using Mass Spectrometric Immunoassay, Journal of Proeteome Research.

Petricoin, Emanuel F., III., et al., Use of Proteomic Patterns in Serum to Identify Ovarian Cancer, The Lancet, 359:572-577, 2002.

Rubenstein, Ken, Ph.D., Post-Genomic Biomarkers: Revolutionizing Drug Development and Diagnostics, D&MD Publications, Report #9129, Sep. 2003.

Danne, et al., Prognostic Implications of Elevated Whole Blood Choline Levels in Acute Coronary Syndromes, American Journal of Cardiology, 91:1060-1067, 2003.

Issaq, et al., The SELDI-TOF MS Approach to Proteomics: Protein Profiling and Biomarker Identification, Biochemical and Biophysical Research Communications 292:587-592, 2002.

"'Peptide' may help predict early heart disease," CNN.com, p. 1-3 (Feb. 12, 2004).

Moss, AJ et al., "Increased Risk of Arrhythmic Events in Long-QT Syndrome with Mutations in the Pore Region of the Human Ether-a-go-go-Related Gene Potassium Channel," *Circulation*, vol. 105, No. 7, p. 794-799 (Feb. 19, 2002).

Fananapazir, et al., Genotype-Phenotype Correlations in Hypertrophic Cardiomyopathy: Insights Provided by Comparisons of Kindreds with Distinct and Identical Beta-myosin Heavy Chain Gene Mutations, Circulation, 1994; 89 (1): 22-32.

Samani, et al., A Meta-analysis of the Association of the Deletion Allele of the Angiotensin-Converting Enzyme Gene with Myocardial Infarction, Circulation, 1996; 94: 708-12.

Aronsky, et al., An Integrated Decision Support System for Diagnosing and Managing Patients with Community-Acquired Pneumonia, Proc. AMIA Symp., 1999; 197-201.

Colombet, et al., Decision Aids for Triage of Patients with Chest Pain: A Systematic Review of Field Evaluation Studies, Proc. AMIA Symp., 1999; 231-35.

Jouven, et al., Predicting Sudden Death in the Population: The Paris Prospective Study I, Circulation, 1999; 99: 1978-83.

Dunn, Studying Heart Disease Using the Proteomic Approach, Drug Discovery Today, Feb. 1, 2000; 5(2): 76-84.

Jouven et al., Circulating Nonesterified Fatty Acid Level as a Predictive Risk Factor for Sudden Death in the Population, Circulation, 2001; 101: 756-61.

Iwasa, et al., Multiple Single-Nucleotide Polymorphisms (SNPS) in the Japanese Population in Six Candidate Genes for Long QT Syndrome, J. Hum. Genet., 2001; 46: 158-62.

Christodoulides, et al., A Microchip-Based Multianalyte Assay System for the Assessment of Cardiac Risk, Analytical Chemistry, 2002; 74(13): 3030-36.

Iwasa, et al., Twenty Single-nucleotide Polymorphisms in Four Genes Encoding Cardiac Ion Channels, J. Hum. Genet., 2002; 47(4): 208-12.

Hirschhorn, et al., A Comprehensive Review of Genetic Association Studies, Genetics in Medicine, 2002; 4(2): 45-61.

Frank-Hansen, et al., Mutations in the Genes KCND2 and KCND3 Encoding the Ion-Channels Conducting the Cardiac Transient Outward Current (ITO) is not a Frequent Cause of Long QT Syndrome, Am. J. Hum. Genet., 2002; 71(4 Supp.): 521.

Hegele, SNP Judgments and Freedom of Association, Arteriosclerosis, Thrombosis, and Vascular Biology, 2002; 22: 1058-61.

Splawski, et al., Variant of SCN5A Sodium Channel Implicated in Risk of Cardiac Arrhythmia, Science, Aug. 23, 2002, 297:1333-36.

NCBI Database SNP [Online], Sep. 7, 2000,refSNP ID: ss1472059.

NCBI Database SNP [Online], Oct. 20, 2000, refSNP ID: rs1538389; & NCBI Database SNP [Online], Oct. 20, 2000, refSNP ID: ss2379946.

NCBI Database SNP [Online], refSNP ID: rs1808973; & NCBI Database SNP [Online], Jan. 2, 2001, refSNP ID: ss2672972.

NCBI Database SNP [Online], refSNP ID: rs730022 & NCBI Database SNP [Online], Sep. 6, 2000, refSNP ID: ss74946.

Dhar et al., Prognostic significance of metastatic lymph node size in patients with gastric cancer, British J. of Surgery, 2003; 90: 1522-30.

Kuzuya et al., Report of the Committee on the classification and diagnostic criteria of diabetes mellitus, Diabetes Res. and Clin. Practice, 2002; 55: 65-85.

METHODS FOR IDENTIFYING PATIENTS AT RISK FOR LIFE THREATENING ARRHYTHMIAS

PRIORITY INFORMATION

The present invention claims priority from U.S. provisional Application No. 60/542,004, filed Feb. 5, 2004.

TECHNICAL FIELD

The present invention relates to a system and method for identifying candidates for receiving cardiac therapy based on biochemical markers associated with propensity for arrhythmias.

BACKGROUND

Sudden cardiac death (SCD), or cardiac arrest, is the sudden, abrupt loss of heart function in a person who may or may not have diagnosed heart disease. Sudden cardiac death may be caused by almost all known heart diseases. Most cardiac arrests occur when the diseased heart begins to exhibit rapid and/or chaotic activity—ventricular tachycardia or fibrillation. Some are due to extreme slowing of the heart. All these events are called life-threatening arrhythmias. Patient's implanted with an implantable medical device, such as an implantable cardioverter defibrillator (ICD), greatly increase their chances of preventing sudden cardiac death caused by sustained ventricular arrhythmias. However, there are a significant number of patients with an increased propensity for suffering sudden cardiac death who have not experienced and survived previous cardiac episodes and therefore who are not already implanted with an implantable medical device. Consequently, there is a need for techniques and apparatus that can identify individuals at risk for sudden cardiac death prior to the onset of identifiable symptoms in order to provide those patients with an appropriate preventative therapy, such as drug therapy and/or an IMD that provides electrical stimulation therapy.

SUMMARY

In general, the invention is directed to systems and techniques for assessing a risk of ventricular tachyarrhythmia in a patient. In some medical conditions, including but not limited to ventricular tachyarrhythmia, certain biochemical factors in the body of the patient reflect the health of a patient. A patient that experiences ventricular tachyarrhythmia, for example, experiences an increased concentration of identifiable proteins in his blood, even the patient is symptom free. By measurement of the concentration of these biochemical markers or "biomarkers" in the patient, an assessment of a risk of ventricular tachyarrhythmia for the patient can be made, based upon the measurements.

In a typical embodiment, the patient submits a sample, such as a blood sample. The sample is tested for one or more biomarkers. Based upon the results of the tests, the patient's risk of ventricular tachyarrhythmia may be assessed.

When a patient has been identified as being at risk of ventricular tachyarrhythmia, the patient may receive therapy to address the risk. The patient may receive drug therapy, for example, or may receive an IMD that provides electrical stimulation therapy. In general, drug therapy prevents a spontaneous induction of a VT or VF episode. An IMD that provides electrical stimulation therapy, by contrast, terminates VT or VF episodes. Patients who receive therapy generally have improved survival rates.

In one embodiment, the invention is directed to a method comprising measuring a biochemical marker in a patient, and assessing a risk of ventricular tachyarrhythmia in the patient as a function of the measurement. This method supports the measurement of any number of biochemical markers and combinations of biochemical markers, and further supports a variety of measurement techniques.

In another embodiment, the invention is directed to a method comprising measuring a biochemical marker in a patient, and assessing a benefit of implanting an electronic cardiac stimulation device in the patient as a function of the measurement. In a further embodiment, the invention is directed to a method comprising measuring one or more biochemical markers in a patient, and assessing a benefit of administering an antiarrhythmic drug to the patient as a function of the measurement.

The invention also includes embodiments in which a computer-readable medium includes instructions for causing a programmable processor to carry out any of the methods of the invention.

In an additional embodiment, the invention presents a system that includes a measuring system configured to measure a biochemical marker in a patient and a processor configured to assess a risk of ventricular tachyarrhythmia in the patient as a function of the measurement. The measuring system may comprise, for example, a mass spectrometer, ELISA tests or any other biochemical assays.

The details of one or more embodiments of the invention are set forth in the accompanying drawings and the description below. Other features, objects, and advantages of the invention will be apparent from the description and drawings, and from the examples.

DETAILED DESCRIPTION

Figure 1:
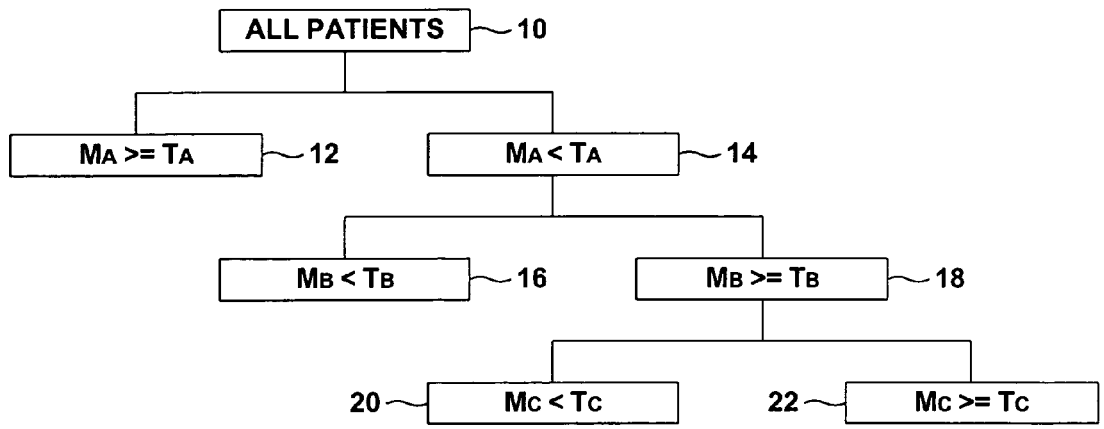
FIG. 1 is a conceptual logical diagram illustrating an embodiment of the invention.

FIG. 1 is a conceptual logical diagram illustrating an embodiment of the invention. Based upon measuring one or more biochemical markers in a group of patients 10, the invention provides for assessing a risk of ventricular tachyarrhythmia in each patient as a function of the measurement.

In the illustration shown in FIG. 1, a "tree analysis" sorts the patients into groups according to measurements of three biochemical markers. The biochemical markers are identified by the letters "A," "B," "C" and "D." Typical biochemical markers include proteins, lipids, genes and peptides or any combination thereof, but the illustration shown in FIG. 1 is not limited to any particular biochemical marker or set of biochemical markers. Specific examples of biochemical markers are discussed below.

For each patient, a measure of a first biochemical marker (denoted $M_A$) is determined. Determining the measure of biochemical marker "A" for a particular patient may include, for example, determining the concentration or mass of biochemical marker "A" in a standard sample of bodily fluid taken from that patient. For each patient, the measure of the first biochemical marker is compared to a threshold value (denoted $T_A$). Those patients for whom $M_A$ is greater than or equal to $T_A$ are deemed to be a group 12 that is not at significant risk of ventricular tachyarrhythmia, and no further testing need be done for the members of group 12. Those patients for whom $M_A$ is less than $T_A$ are deemed to be a group 14 that may be, or may not be, at risk of ventricular tachyarrhythmia. In FIG. 1, the members of group 14 undergo further testing to determine the individual members' risks of ventricular tachyarrhythmia.

For each patient in group 14, a measure of a second biochemical marker "B" (denoted $M_B$) is determined. For each patient in group 14, the measure of the second biochemical marker is compared to a second threshold value (denoted $T_B$). Those patients for whom $M_B$ is less than $T_B$ are deemed to be a group 16 that is not at significant risk of ventricular tachyarrhythmia, and no further testing need be done for the members of group 16. Those patients for whom $M_B$ is greater than or equal to $T_B$ are deemed to be a group 18 that may be, or may not be, at risk of ventricular tachyarrhythmia.

The members of group 18 undergo further testing with respect to a measure of a third biochemical marker "C" (denoted $M_C$). For each patient in group 18, the measure of the third biochemical marker is compared to a third threshold value (denoted $T_C$). On the basis of the comparison, the patients are divided into a group 20 that is not at significant risk of ventricular tachyarrhythmia, and a group 22 that is at significant risk of ventricular tachyarrhythmia.

In other words, FIG. 1 illustrates assessing a risk of ventricular tachyarrhythmia for a patient as a function of the measurement of three biochemical markers. Unless a patient meets the threshold criteria for all three biochemical markers, the patient will not be deemed to be at significant risk of ventricular tachyarrhythmia.

The thresholds $T_A$, $T_B$ and $T_C$ are determined empirically. Clinical studies and experience may be used to determine thresholds for each biochemical marker. The thresholds may differ from marker to marker. For some biochemical markers, a patient may be at higher risk when the measure of the biochemical marker is above the threshold, and for other biochemical markers, the patient may be at higher risk when the measure of the biochemical marker is below the threshold.

Figure 2:
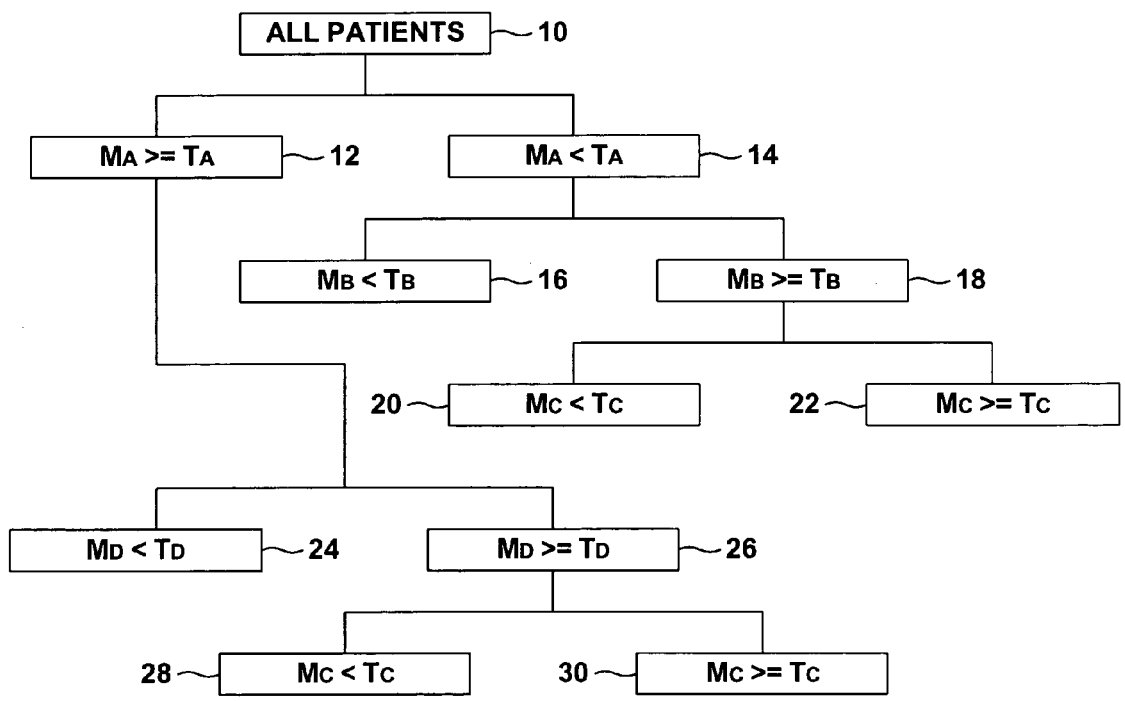
FIG. 2 is a conceptual logical diagram illustrating a variation of the embodiment of the invention shown in FIG. 1.

FIG. 2 is a conceptual logical diagram illustrating an embodiment of the invention that is a variation of the technique illustrated in FIG. 1. Unlike FIG. 1, patients sorted into group 12 are subjected to further testing. For each patient in group 12, a measure of a fourth biochemical marker "D" (denoted $M_D$) is determined, and the measure is compared to a fourth threshold value (denoted $T_D$). On the basis of this comparison, patients in group 12 are sorted into groups 24 and 26. Those patients in group 24 are deemed to be not at significant risk of ventricular tachyarrhythmia, and no further testing need be done for the members of group 24.

Those patients in group 26, however, are subjected to further testing. The members of group 26 undergo further testing with respect to the third biochemical marker "C," just like the members of group 18. On the basis of a comparison of the measure of the third biochemical marker to the third threshold, the patients in group 26 are divided into a group 28 that is not at significant risk of ventricular tachyarrhythmia, and a group 30 that is at significant risk of ventricular tachyarrhythmia.

In other words, FIG. 2 illustrates assessing a risk of ventricular tachyarrhythmia for a patient as a function of the measurement of four biochemical markers. A patient may be deemed to be at significant risk of ventricular tachyarrhythmia according to more than one testing path.

Figure 3:
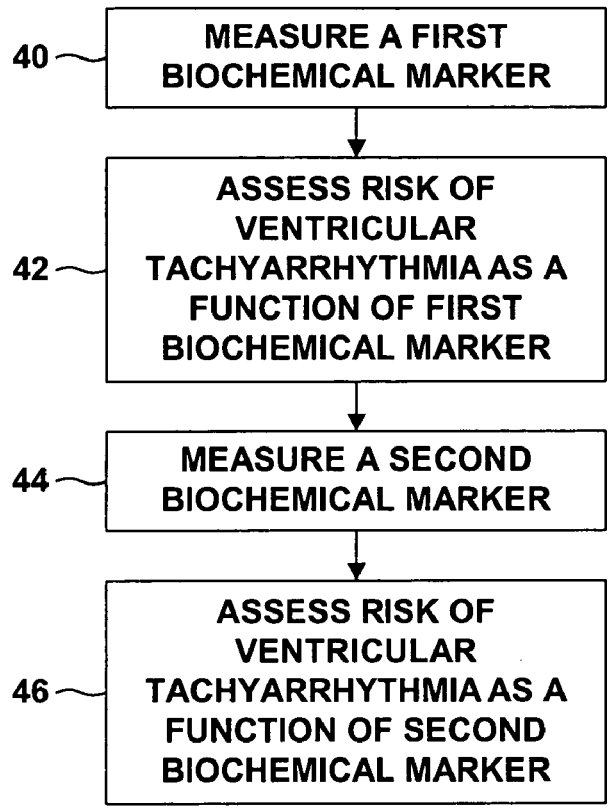
FIGS. 3 and 4 are flow diagrams illustrating techniques for assessment of risk of ventricular tachyarrhythmia.

FIG. 3 is a flow diagram illustrating logical sorting embodiments such as are depicted in FIGS. 1 and 2. An apparatus, such as apparatus illustrated in FIGS. 5 and 6, or a technician measures a first biological marker (40) and assesses a risk of ventricular tachyarrhythmia in the patient as a function of the measurement (42). The apparatus or technician measures a second biological marker (44) and assesses the risk of ventricular tachyarrhythmia in the patient as a function of that measurement (46).

Figure 4:
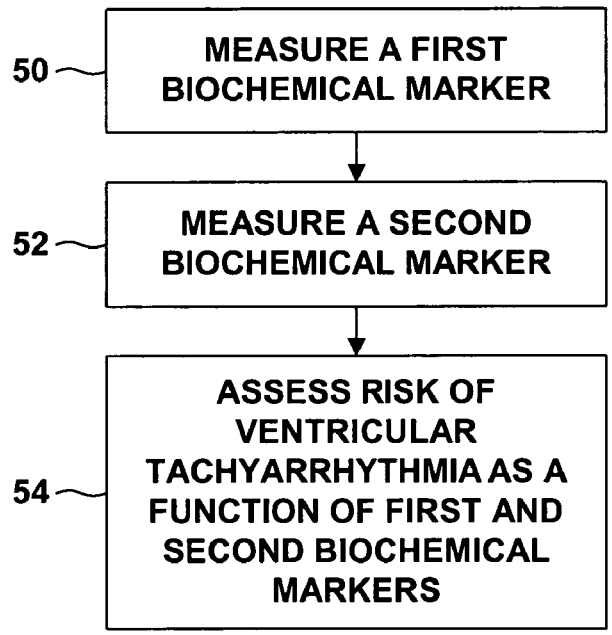

In the procedure outlined in FIG. 4, the apparatus or technician measures a first biological marker (50) and measures a second biological marker (52), and assesses the risk of ventricular tachyarrhythmia in the patient as a function of both measurements (54). The techniques shown in FIGS. 3 and 4 may achieve the same result, that is, a patient may be sorted according to risk of ventricular tachyarrhythmia using either technique. When a patient is deemed to be at risk, an appropriate therapy may be applied. Therapy for a patient may include, for example, implanting an electronic cardiac stimulation device in the patient that terminates episodes of ventricular tachyarrhythmia or administering an antiarrhythmic drug that prevents induction of such episodes.

Figure 5:
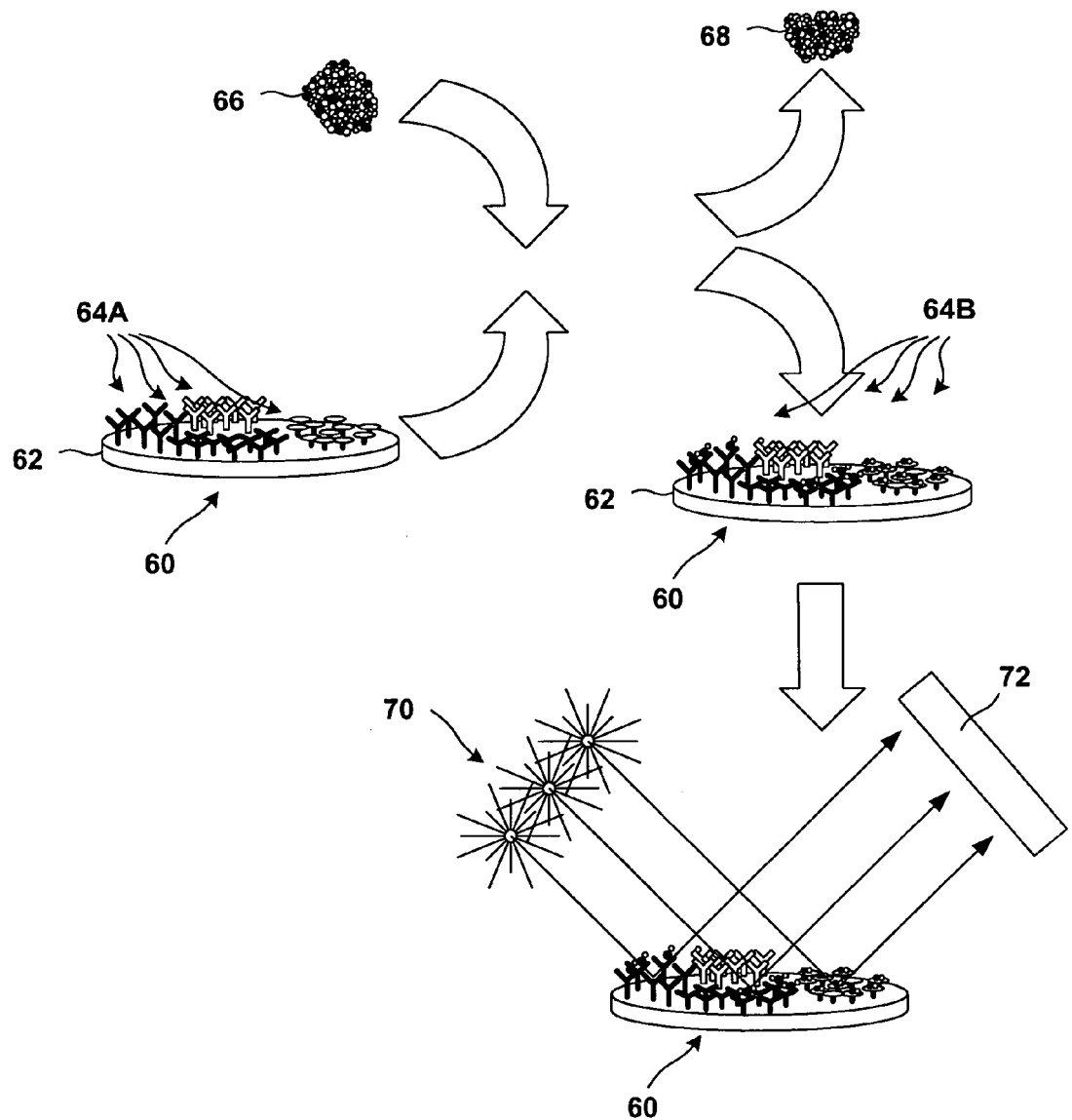
FIG. 5 is a conceptual diagram illustrating a technique for mass analysis of a sample for biochemical markers.

FIG. 5 is a conceptual diagram illustrating a technique for measuring a plurality of biological markers. A biochip 60 comprises a substrate 62 and one or more sensing elements 64A. In FIG. 5, four distinct sensing elements are coupled to substrate 62, but the invention encompasses use of any number of sensing elements.

Biochip 60 is a set of miniaturized test sites, or microarrays, arranged on a solid substrate 62 made from a material such as silicone or glass. Each test site includes a set of sensing elements 64A. In general, sensing elements include one or more components that change conformation in the presence of an analyte of interest. Typical sensing elements include antibody molecules that change conformation in the presence of a specific biomarker, but that do not change conformation in the presence of any other biomarker. The invention encompasses any sensing element, however, and is not restricted to antibodies. The sensing elements of biochip 60 may have general properties such as high affinity toward hydrophilic or hydrophobic molecules, or anionic or cationic proteins, for example.

Substrate 62 may have a surface area of about one square centimeter, but the invention encompasses biochips that are larger or smaller. Substrate 62 may be formed in any shape, may include any number of test sites, and may include any combination of sensing elements. The invention is not limited to any particular biochip.

Biochip 60 is exposed to sample 66. Sample 66 may include any biological sample from a patient, such as a blood sample. Biomarkers present in sample 66 react with sensing elements on biochip 60. Exposed sensing elements 64B typically react with biomarkers in sample 66 by undergoing a conformational change, or by forming ionic, covalent or hydrogen bonds. The unreacted or unbound portion of sample 68 is washed away.

The concentrations of biomarkers in sample 66 are a function of the extent of the reaction between exposed sensing elements 64 and sample 66. The extent of the reaction is determinable by, for example, mass spectrometry. The Surface Enhanced Laser Desorption/Ionization (SELDI) process is an example of a mass spectrometry technique for determining the concentrations of biomarkers.

In general, the SELDI process directs light generated by one or more light sources 70 at biochip 60. A mass analyzer 72 measures the molecular weight of the biomarkers. In particular, biomarkers on biochip 60 are ionized and separated, and molecular ions are measured according to their mass-to-charge ratio (m/z). Ions are generated in the ionization source by inducing either the loss or the gain of a charge (e.g. electron ejection, protonation, or deprotonation). Once the ions are formed in the gas phase they can be electrostatically directed into mass analyzer 72, separated according to their mass and finally detected.

Proteins bound to sensing elements 64B, for example, can be ionized and separated based on molecular properties, such as being hydrophilic versus hydrophobic. Proteins captured by sensing elements 64B are freed by the energy provided by a weak laser pulse, and charged positively by the removal of a second electron as a result of illumination by a second laser pulse. Time of flight though a vacuum tube following acceleration in an electric field allows the measurement of the mass-to-charge ratio.

The invention supports other techniques for determining the concentrations of biomarkers, and is not limited to the SELDI process. In one embodiment, for example, the techniques of the invention could be carried out by using conventional assays for individual biomarkers, such as an Enzyme Linked ImmunoSorbent Assay (ELISA tests). An advantage of using a biochip is that a biochip saves time and effort in comparison to individual assays when multiple markers are to be measured.

Many protein markers are generally accepted as being indicative of cardiac conditions. C-Reactive Protein (CRP) is associated with sudden cardiac death, Fatty Acid Binding Protein is a plasma marker associated with acute myocardial infarction, Cardiac Troponin is associated with myocardial infarction, Myosin Light and Heavy Chains are associated with heart failure, brain natriuretic peptide (BNP) is associated with left ventricular heart failure, and so on.

Other markers may be associated with other cardiac conditions of interest. The markers may be identified by their name, or by other characteristics, such as molecular weight.

In an example clinical study, patients with coronary artery disease were divided into two groups: a test group that had coronary artery disease, and an implantable medical device (with one sustained VT/VF episode with cycle length less than or equal to 400 ms); and a control group having coronary artery disease but no implantable medical device, and no known history of VT/VF. In the study, sixteen patients had an IMD and thirty-two were in the control group. Certain patients were excluded from the study, including non-Caucasians, females, patients outside of age limit of 45-80, and patients having certain health problems or cardiac conditions. Patients meeting the inclusion criteria were enrolled in the study. Upon enrollment, an extensive questionnaire, including medical history was filled.

Three blood samples were drawn from each patient. At least one sample comprised 8.5 mL blood drawn from the patients for serum separation. Serum is the cell free portion of the blood containing proteins and lipids. At least one other sample of an additional 12 mL blood was drawn and kept as whole blood for eventual genetic analysis. The samples were analyzed using proteomic and lipidomic techniques.

During processing, proteins in the serum were fractionated into 4 distinct groups based on the pH (acidity) of the protein. Later on, these proteins were spotted onto three surfaces of one or more biochips. The surfaces had different chemical affinities. A surface designated "CM10" was responsive to weak cation exchange surface. A surface designated "H50" was a hydrophobic surface. A surface designated "IMAC" was an immobilized metal affinity surface. The SELDI time-of-flight technique was used to measure the molecular weight of the proteins on each surface.

Figure 6:
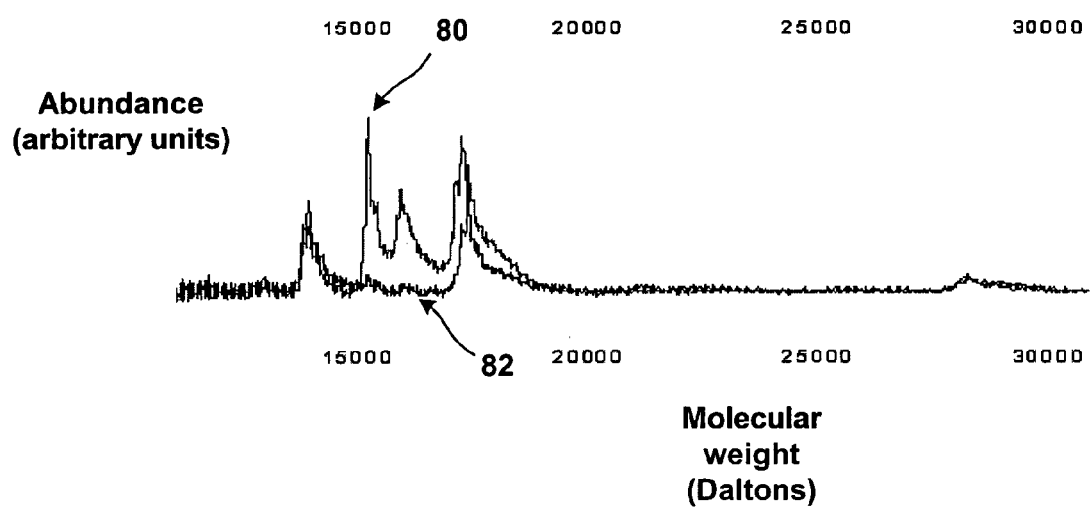
FIG. 6 is a graph showing differences in biochemical marker abundance for a patient at risk of ventricular tachyarrhythmia, compared to a patient in a control group.

FIG. 6 shows the results of sample proteomic spectra of two patients, one having an IMD (80) and one in the control (82). These results indicate that some of the protein markers in the blood were expressed differently in two groups. Data produced by processing of all of patients followed similar patterns, i.e., the data indicated that some of the protein markers in the blood obtained from patients were expressed differently in two groups. The differences in markers may form a basis for distinguishing the patients that would benefit from an IMD from the patients that would not benefit.

Figure 7:
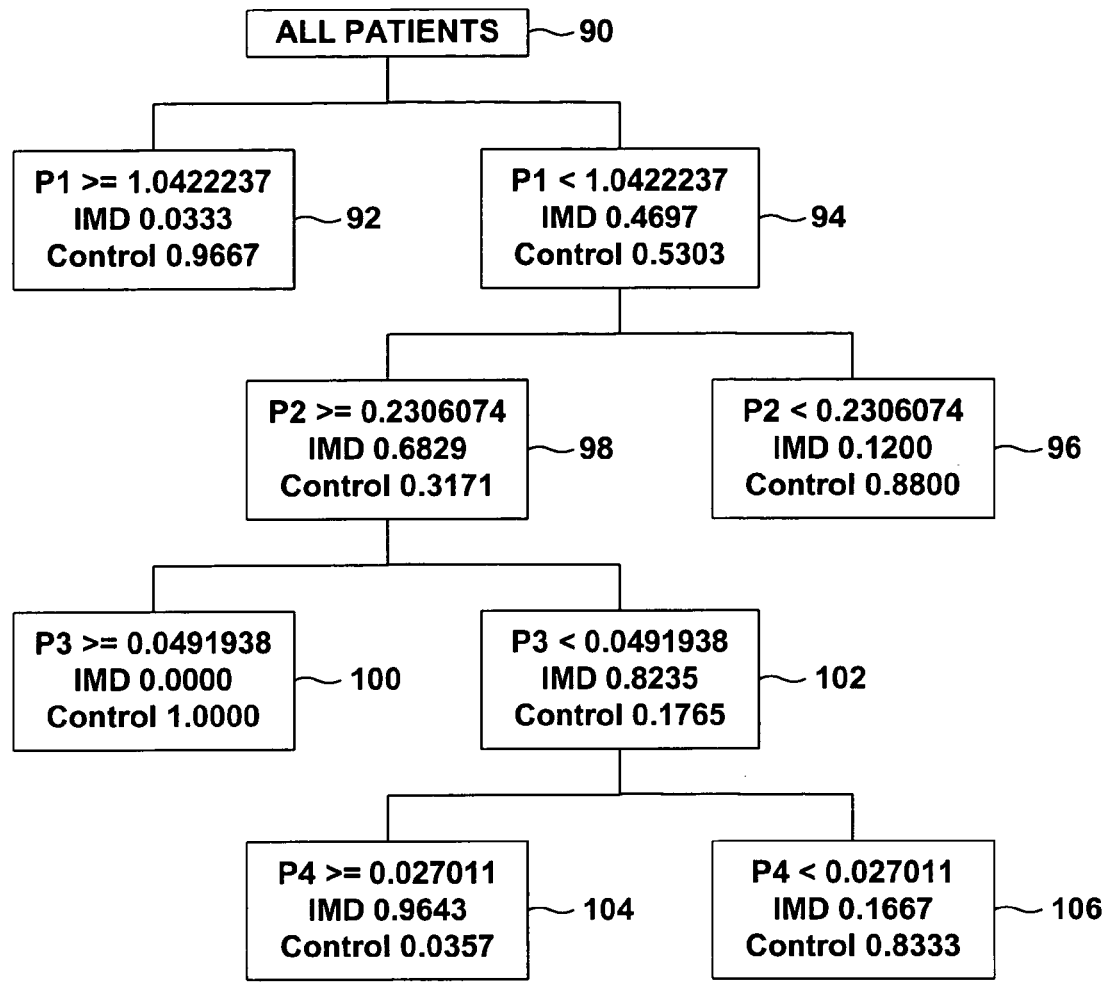
FIG. 7 is a logical diagram illustrating a technique for sorting patients at risk of ventricular tachyarrhythmia from a control group.

FIG. 7 shows a tree analysis applied to these results to identify potential biomarkers that differentiate patients who have a higher propensity for fatal ventricular arrhythmias from the others. As a result of the tree analysis, four protein markers could be used to classify the 48 patients correctly. Specifics of these protein markers are shown in table below:

| Protein Number | Molecular Weight (Da) | Isoelectric pH (pI) | Capture Surface |
|---|---|---|---|
| P1 | 10,146.5 | 9+ | CM10 weak cation exchange) |
| P2 | 15,006 | 9+ | CM10 weak cation exchange) |
| P3 | 166,582 | 5-7 | CM10 weak cation exchange) |
| P4 | 10,948 | 9+ | IMAC (Immobilized Ion Affinity Surface) |
| P5 | 11,991 | 5-7 | Immobilized Metal Affinity Surface |
| P6 | 10,552.4 | 9 | Weak Cation Exchange Surface |
| P7 | 43,529.4 | 9 | Weak Cation Exchange Surface |
| P8 | 13,806.8 | 9 | Hydrophobic Surface |

In the above table, proteins are identified by a number and are characterized by a molecular weight in Daltons and an Isoelectric pH (pI). The molecular weight in Daltons is not necessarily unique to any particular protein, but proteins are often distinguishable by molecular weight. It is not necessary to the invention that the protein having that molecular weight and/or pi be specifically identified by name or by amino-acid sequence.

As shown in FIG. 7, the amount of protein P1 in the serum was tested for all patients 90. Patients 92 having an abundance of P1 greater than or equal to 1.0422237 (measured in arbitrary units) were not at significant risk of ventricular tachyarrhythmia were therefore not candidates for an IMD. Patients 94 having an abundance of P1 less than 1.0422237, however, could not be classified by abundance of P1 alone.

For patients 94, the amount of protein P2 in the serum was tested. Patients 96 having an abundance of P2 less than 0.2306074 were not candidates for an IMD. Patients 98 having an abundance of P2 greater than or equal to 0.2306074 were tested for protein P3. Patients 100 having an abundance of P3 greater than or equal to 0.0491938 were not candidates for an IMD, while patients 102 having an abundance of P3 less than 0.0491938 were tested for protein P4. Patients 104 having an abundance of P4 greater than 0.027011 were considered to be candidates for an IMD, while the remaining patients 106 were not considered to be candidates for an IMD.

The arbitrary units may be normalized to an abundant protein, such as albumin, which is generally consistent in relative abundance among a group of patients. The invention supports the use of other benchmarks as well, such as the total ion current in the mass spectrometer used to measure the protein abundance.

In addition, the invention supports a range of measurement standards. In some cases, it is not feasible to perform measurements that have one hundred percent sensitivity and specificity, and some standards may be applied to determine whether a patient is at significant risk of ventricular tachyarrhythmia or not. The tree analysis depicted in FIG. 7, for example, is generally more sensitive and specific than conventional patient sorting techniques (such as a signal averaged electrocardiogram), even though it may result in some false positives and false negatives.

The tree shown in FIG. 7 may be generated using Classification and Regression Tree (CART) analysis. The tree analysis depicted in FIG. 7 is an example of an approach for assessing a risk of ventricular tachyarrhythmia in one or more patients as a function of a measurement of one or more biochemical markers. The assessment may be performed in other ways as well. The test may be expressed as logical test such as an IF-THEN test, which can be implemented in software:

IF
    (($P1<1.0422237$) AND ($P2 \geq 20.2306074$) AND ($P3<0.0491928$) AND ($P4>0.027011$))

THEN
    PATIENT IS AN IMD CANDIDATE

This IF-THEN test gave the following results when applied to the clinical data where two samples from each patient were processed:

|  | VT/VF | NORMAL |
| --- | --- | --- |
| TEST (+) | 27 | 1 |
| TEST (−) | 5 | 63 |

Sensitivity: $27/(27 + 5) = 84\%$
Specificity: $63/(63 + 1) = 98\%$
False Positives: $1/(1 + 27) = 4\%$
False Negatives: $5/(5 + 63) = 7\%$ Using conventional sorting techniques, sensitivity and specificity tend to be around 55 to 75 percent. This clinical data demonstrates an improvement in sensitivity and specificity in comparison to conventional techniques.

Another technique for assessing a risk of ventricular tachyarrhythmia in one or more patients as a function of a measurement of one or more biochemical markers is to use an artificial neural network. In an exemplary application, the clinical data were analyzed using an artificial neural network having four input nodes corresponding to proteins P1, P2, P3 and P4. The network included four hidden nodes and one output. This artificial neural network gave the following results when applied to the clinical data where two samples from each patient was processed:

|  | VT/VF | NORMAL |
| --- | --- | --- |
| TEST (+) | 24 | 1 |
| TEST (−) | 8 | 63 |

Sensitivity: $24/(24 + 8) = 75\%$
Specificity: $63/(63 + 1) = 98\%$
False Positives: $1/(1 + 25) = 4\%$
False Negatives: $8/(8 + 63) = 11\%$ The test procedures described above are not unique, nor are they necessarily the most efficient method of sorting patients who are candidates for an IMD from those that are not. Nevertheless, these procedures are illustrations of tests that can be used to screen patients to find out the ones who have a propensity for ventricular tachyarrhythmia, and thus may be at increased risk of sudden cardiac death.

Depending upon the biochemical markers of interest, measurements of mass, concentration or abundance may be less important than determination of whether the marker is present or absent. The invention encompasses embodiments in which measurement of a biochemical marker in a patient includes determining whether the marker is present or not. For example, animal experimentation may establish that animals suffering sudden cardiac death exhibit an absence of a set of proteins and peptides having particular molecular weights. Similarly, animal experimentation may establish that animals suffering sudden cardiac death exhibit proteins or peptides that are otherwise not present. Detection of the presence or absence of such proteins or peptides in a human sample may have clinical significance, as the presence or absence proteins or peptides may be indicative of risk of sudden cardiac death.

In some cases, what is of interest is not the presence or absence of a biochemical marker, or its concentration on a single occasion, but an increase or decrease in the concentration or the rate of change, as demonstrated by two or more measurements separated by a time interval such as two weeks or one month. The invention supports consideration of change as a basis for assessing a risk of ventricular tachyarrhythmia.

Figure 8:
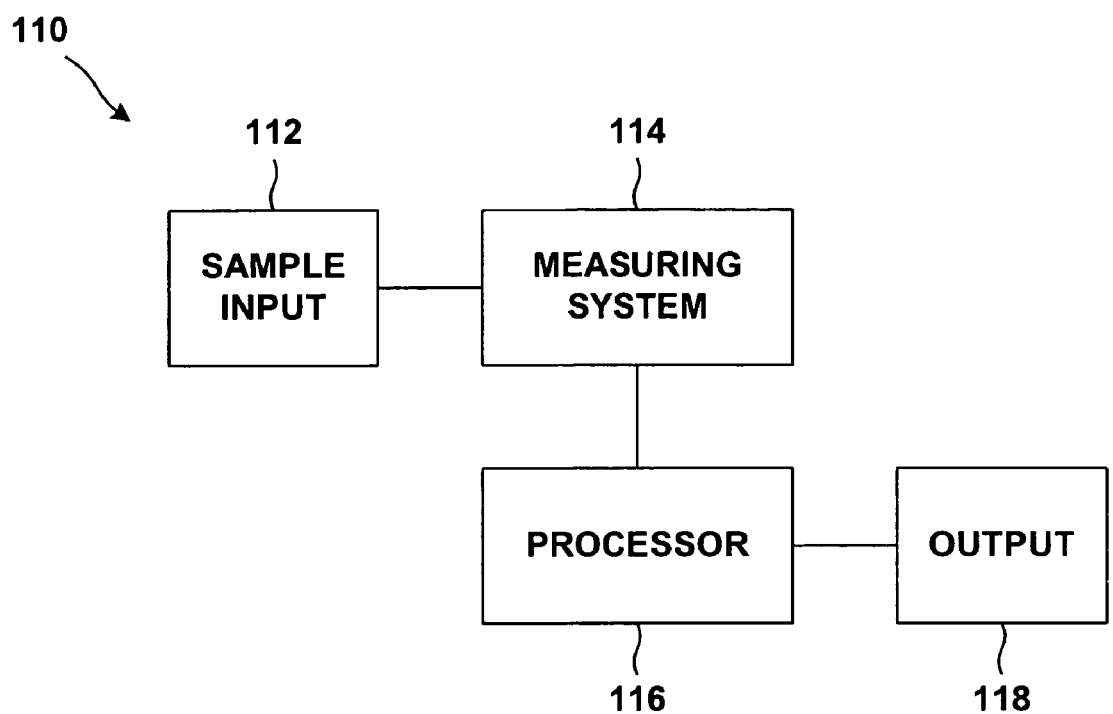
FIG. 8 is a block diagram of a system configured to carry out an embodiment of the invention.

Test procedures such as the exemplary procedures described above can be automated, in whole or in part. FIG. 8 is an example of a system 110 that can perform an automated analysis of biochemical markers and can assess a risk of ventricular tachyarrhythmia in a patient as a function of the analysis. System 110 includes a sample input module 112, which receives a sample for analysis, and a measuring system 114. In one embodiment of the invention, input module 112 may include one or more biochips like those depicted in FIG. 5, and measuring system 114 may comprise a SELDI-based mass analyzer. The invention is not limited to such components, however.

A processor 116 receives the measurements from measuring system 114 and assessing a risk of ventricular tachyarrhythmia in the patient as a function by analyzing the measurements. Processor 116 may apply a tree analysis, such as the analyses depicted in FIGS. 1, 2 and 7, to determine whether a patient is at risk of ventricular tachyarrhythmia. Processor 116 may further assess a benefit of implanting a medical device in the patient as a function of the measurements, or administering an antiarrhythmic drug to the patient.

An output module 118 reports the results of the analysis. Output module 118 may comprise a display screen, printer, or any other device that reports the results of the analysis. A benefit of implanting a medical device in the patient as a function of the measurement is assessed.

The invention may offer one or more advantages. Clinical data suggest that, in a significant number of cases, sudden cardiac death is the result of VT or VF. Episodes of VT or VF are treatable with an IMD or medication. The invention presents techniques for identifying the patients who are at risk of experiencing ventricular tachyarrhythmia. As a result, there is an improved chance that these patients will receive life-saving therapy, thereby reducing their risk of sudden cardiac death.

Therapies involving an IMD or medication need not be exclusive of one another. Furthermore, the invention supports therapies in addition to implantation of an IMD or regulation of a regimen of medication. In some circumstances, the biomarkers may be more than symptomatic or indicative of the risk of VT or VF, and may be substantially causally related to the risk of VT or VF. In such circumstances, therapy may be directed to the biomarkers.

It may be possible, for example, to treat the patient by adjusting the concentration of biomarkers. When a concentration of certain protein biomarkers is found to be lower in a patient with VT or VF, then perhaps the patient can be treated by injecting those proteins into the blood, thereby restoring a more healthful concentration of the biomarkers. Conversely, when a concentration of certain protein biomarkers is found to be higher, then perhaps the patient can be treated by reducing the concentration of the protein biomarkers. A high concentration can be reduced by, for example, injection of enzymes that cleave or inhibit the activity of one or more protein biomarkers. Similarly, gene therapy can be used to alter protein and gene expression levels. Consequently, application of therapy may include determining one or more proteins or one or more genes, or a combination thereof, to be delivered to the patient.

The techniques of the invention may call for sample from the patient. In many embodiments, the sample is one that is taken as a matter of course in a medical examination, such as a blood sample.

Further, the invention should reduce the incidents of false positives and false negatives. As a result, there is a better chance that patients that can benefit from an IMD will have a chance to receive an IMD. In addition, the invention includes the capability of being self-improving. As more clinical data are collected, different or more detailed tree analyses or other sorting techniques may be developed. Empirical experience may make tests more sensitive and more specific.

Various embodiments of the invention have been described. Various modifications can be made to the described embodiments without departing from the scope of the invention. For example, the invention is not limited to consideration of biochemical markers exclusively. The assessment of risk of ventricular tachyarrhythmia in the patient may also be a function of other measurable physiological factors. Electrophysiological measurements, such as an electrocardiogram, and hemodynamic factors, such as a measurement of ejection fraction, may be taken into consideration. System 110 in FIG. 8 may further include a sensor to measure a physiological factor, and processor 116 may assess a risk of ventricular tachyarrhythmia as a function of the measurement of the physiological factor.

Although the invention has been described with proteins as biochemical markers, the invention is not limited to proteins. The invention also supports consideration of other markers, such as genetic markers, lipid markers and lipoprotein markers. The markers may be considered alone or in combination. For example, the invention supports risk assessments as a function of combinations of gene and protein markers. Techniques such as nuclear magnetic resonance, gene sequencing, or single nucleotide polymorphism (SNP) may be used to identify these markers. Consideration of markers such as these may result in enhanced sensitivity and specificity.

Analysis can be done using multiple techniques. In addition to generating a sorting tree, applying a logical analysis such as an IF-THEN statement, and artificial neural networks, one can assess a risk of ventricular tachyarrhythmia using linear clustering techniques (e.g. proximity, similarity, dissimilarity, weighted proximity, and principle component analysis), non-linear clustering techniques (e.g. artificial neural networks, Kohonen networks, pattern recognizers and empirical curve fitting), as well as logical procedures (e.g. CART, partition and hierarchical clustering algorithms). The invention is not limited to these techniques, however, and encompasses other linear analysis, non-linear analysis, logical analysis and conditional techniques.

Some of the techniques described above may be embodied as a computer-readable medium comprising instructions for a programmable processor such as processor 116 in FIG. 8. The programmable processor may include one or more individual processors, which may act independently or in concert. A "computer-readable medium" includes but is not limited to read-only memory, Flash memory and a magnetic or optical storage medium.

We claim:

1. A method for assessing a risk of ventricular tachyarrhythmia in a patient using a plurality of biochemical markers, comprising the steps of:
   assessing the risk of ventricular tachyarrhythmia in the patient as a function of a measurement of a first biochemical marker A in the patient;
   assessing the risk of ventricular tachyarrhythmia as a function of a measurement of a second biochemical marker B in the patient;
   comparing a measure $M_A$ of the first biochemical marker A to a threshold value $T_A$ of A, wherein if $M_A$ is greater than or equal to $T_A$, a risk of ventricular tachyarrhythmia does not exist in a patient, and wherein if $M_A$ is less than $T_A$, a risk of ventricular tachyarrhythmia may or may not exist in said patient, and wherein if $M_A$ is less than $T_A$, comparing a measure $M_B$ of the second biochemical marker B to a threshold value $T_B$ of B, wherein if $M_B$ is less than $T_B$ a risk of ventricular tachyarrhythmia does not exist in the patient, and wherein if $M_B$ is greater than or equal to $T_B$, a risk of ventricular tachyarrhythmia may or may not exist in the patient.

2. The method according to claim 1, wherein a benefit of administering a drug to the patient as a function of the measurement of the biochemical markers is assessed.

3. The method according to claim 1, wherein assessing the risk of ventricular tachyarrhythmia comprises one of generating a sorting tree, generating a logical test, generating an artificial neural network, and assessing the risk of at least one of ventricular tachycardia, ventricular fibrillation, and sudden cardiac death.

4. The method according to claim 1, wherein measuring the biochemical markers comprises one of measuring a mass of the biochemical markers, measuring a mass-to-charge ratio of the biochemical marker with a mass spectrometer, and measuring an isoelectric pH of the biochemical markers.

5. The method according to claim 1, wherein the biochemical markers comprises one of a protein, a lipid and a gene.

6. The method according to claim 1, further comprising:
   measuring a physiological factor of the patient; and
   assessing the risk of ventricular tachyarrhythmia in the patient as a function of the measurement of the physiological factor.

7. The method according to claim 6, wherein the physiological factor comprises at least one of an electrophysiological factor and a hemodynamic factor.

8. The method according to claim 1, further comprising one of assessing a benefit of implanting a medical device in the patient as a function of the measurements, and assessing a benefit of administering an antiarrhythmic drug to the patient as a function of the measurements.

9. The method according to claim 8, wherein the medical device comprises at least one of an electronic cardiac stimulation device and a drug delivery device.

10. The method according to claim 1, further comprising:
exposing a biochip to a biological sample from a patient, the biochip comprising a plurality of sensing elements; and
assessing the risk of ventricular tachyarrhythmia in the patient as a function of a reaction between the sample and the sensing elements.

11. The method of claim 10, wherein assessing the risk of ventricular tachyarrhythmia in the patient as a function of a reaction between the sample and the sensing elements comprises performing mass spectrometry on the biochip.

12. The method of claim 11, wherein performing the mass spectroscopy comprises performing a Surface Enhanced Laser Desorption/Ionization process.

13. The method of claim 1, wherein measuring the biochemical markers comprises one of determining one of the presence and the absence of the biochemical markers, and determining a change of concentration of the biochemical markers.

14. The method of claim 1, further comprising applying a therapy as a function of the assessment.

15. The method of claim 14, wherein applying a therapy comprises one of implanting an electronic cardiac stimulation device in the patient, administering an antiarrhythmic drug to the patient, and determining at least one of a protein and a gene to be delivered to the patient.

16. The method of claim 1, wherein if $M_B$ is greater than or equal to $T_B$, further comprising the step of:
comparing a measure $M_C$ of a biochemical marker C to a threshold value $T_C$ of C, wherein if $M_C$ is less than $T_C$, a risk of ventricular tachyarrhythmia does not exist in the patient, and wherein if $M_C$ is greater than or equal to $T_C$, a risk of ventricular tachyarrhythmia may or may not exist in the patient.

17. The method of claim 1, wherein if $M_A$ is greater than or equal to $T_A$, further comprising the step of:
comparing a measure $M_D$ of a biochemical marker D to a threshold value $T_D$ of D, wherein if $M_D$ is less than $T_D$, a risk of ventricular tachyarrhythmia does not exist in the patient, and wherein if $M_D$ is greater than or equal to $T_D$, a risk of ventricular tachyarrhythmia may or may not exist in the patient.

18. The method of claim 17, wherein if $M_D$ is greater than or equal to $T_D$, further comprising the step of:
comparing a measure $M_C$ of a biochemical marker C to a threshold value $T_C$ of C, wherein if $M_C$ is less than $T_C$, a risk of ventricular tachyarrhythmia does not exist in the patient, and wherein if $M_C$ is greater than or equal to $T_C$, a risk of ventricular tachyarrhythmia may or may not exist in the patient.

19. The method of claim 1, further comprising the step of:
comparing a plurality of biochemical biomarkers P1, P2, P3 and P4 in a patient, wherein
P1 is a protein having a Molecular Weight (Da) of 10,146.5 and an Isoelectric pH (pI) of 9+ and a Capture Surface of a weak cation exchange (CM 10),
P2 is a protein having a Molecular Weight (Da) of 15,006 and an Isoelectric pH (pI) of 9+ and a Capture Surface of a weak cation exchange (CM 10),
P3 is a protein having a Molecular Weight (Da) of 166, 582 and an Isoelectric pH (pI) of 5-7 and a Capture Surface of a weak cation exchange (CM 10), and
P4 is a protein having a Molecular Weight (Da) of 10,948 and an Isoelectric pH (pI) of 9+ and a Capture Surface of an Immobilized Ion Affinity Surface (IMAC).

20. The method of claim 19, further comprising the step of: evaluating in the patient an amount of P1 where if P1 is greater than or equal to 1.0422237 in arbitrary units, the patient is not at significant risk of ventricular tachyarrhythmia, and where if P1 is less than 1.0422237, the patient may be at risk of ventricular tachyarrhythmia.

21. The method of claim 20, further comprising the step of: evaluating in the patient an amount of P2 where if P2 is greater than or equal to 0.2306074 in arbitrary units, the patient may be at significant risk of ventricular tachyarrhythmia, and where if P2 is less than 0.2306074, the patient is not at risk of ventricular tachyarrhythmia.

22. The method of claim 21, further comprising the step of: evaluating in the patient an amount of P3 where if P3 is greater than or equal to 0.049 1938 in arbitrary units, the patient is not at significant risk of ventricular tachyarrhythmia, and where if P3 is less than 0.049 1938, the patient may be at risk of ventricular tachyarrhythmia.

23. The method of claim 22, further comprising the step of: evaluating in the patient an amount of P4 where if P4 is greater than or equal to 0.027011 in arbitrary units, the patient is a candidate for an Implantable Medical Device, and where if P4 is less than 0.027011, the patient is not a candidate for an Implantable Medical Device.

24. The method according to claim 1, wherein a benefit of implanting a medical device in the patient as a function of the measurement of the biochemical markers is assessed.

* * * * *

UNITED STATES PATENT AND TRADEMARK OFFICE
CERTIFICATE OF CORRECTION

PATENT NO.        : 7,622,303 B2                                           Page 1 of 1
APPLICATION NO.   : 11/050611
DATED             : November 24, 2009
INVENTOR(S)       : Soykan et al.

It is certified that error appears in the above-identified patent and that said Letters Patent is hereby corrected as shown below:

Column 6, line 48, the term "Isoelectric pH (p1)" should read --Isoelectric pH (pI)--; line 52, "pi" should read --pI--.

Column 10, line 43, insert a comma after the text "less than $T_B$".

Claim 22, col. 12, lines 39 and 41, delete the space in the number "0.049 1938", each occurrence, to read --0.0491938--.

Signed and Sealed this

Ninth Day of February, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,622,303 B2 | Page 1 of 1 |
| APPLICATION NO. | : 11/050611 | |
| DATED | : November 24, 2009 | |
| INVENTOR(S) | : Orhan Soykan | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1271 days.

Signed and Sealed this
Thirty-first Day of May, 2011

David J. Kappos
*Director of the United States Patent and Trademark Office*